(12) United States Patent
Schroeder et al.

(10) Patent No.: US 10,962,483 B2
(45) Date of Patent: Mar. 30, 2021

(54) REDUCTION OF MOLECULAR BACKGROUND EMISSION AND SAMPLE MATRIX MANAGEMENT IN A SOLUTION CATHODE GLOW DISCHARGE

(71) Applicant: InnoTech Alberta Inc., Edmonton (CA)

(72) Inventors: Stuart Garth Schroeder, Sherwood Park (CA); Wade Joseph Hagman, Spruce Grove (CA)

(73) Assignee: InnoTech Alberta Inc., Edmonton (CA)

( * ) Notice: Subject to any disclaimer, the term of this patent is extended or adjusted under 35 U.S.C. 154(b) by 0 days.

(21) Appl. No.: 16/151,034

(22) Filed: Oct. 3, 2018

(65) Prior Publication Data

US 2019/0101493 A1    Apr. 4, 2019

Related U.S. Application Data

(60) Provisional application No. 62/567,278, filed on Oct. 3, 2017.

(51) Int. Cl.
*G01N 21/67* (2006.01)
*G01N 27/62* (2021.01)
(Continued)

(52) U.S. Cl.
CPC .............. *G01N 21/67* (2013.01); *G01N 21/69* (2013.01); *G01N 27/62* (2013.01); *G01N 33/50* (2013.01); *H05H 1/48* (2013.01)

(58) Field of Classification Search
CPC ........... G01N 21/67; G01N 27/62; H05H 1/48
See application file for complete search history.

(56) References Cited

U.S. PATENT DOCUMENTS 3,949,260 A * 4/1976 Bayless .................. H01J 3/025
                                                                313/157
6,758,941 B1 * 7/2004 Ookawa ............ H01J 37/32082
                                                                118/723 E
(Continued)

FOREIGN PATENT DOCUMENTS

CA         2998750 A1    3/2017
CN       204154649 U     2/2015
(Continued)

OTHER PUBLICATIONS

Todd A. Doroski, "Solution—cathode glow discharge—optical emission spectrometry of a new design and using a compact spectrograph†",Anal. At. Spectrom., 2013 (Year: 2013).*

(Continued)

*Primary Examiner* — Maurice C Smith
(74) *Attorney, Agent, or Firm* — Borden Ladner Gervais LLP; Tim Webb

(57) ABSTRACT

A device and method to reduce molecular background emission and to increase matrix management in solution cathode glow discharge (SCGD). A purging device for purging atmospheric gases from a solution cathode glow discharge (SCGD) apparatus, comprising a hollow body that encloses a plasma generated between a solid anode and a solution cathode, wherein the body comprises at least one opening for release of water vapor generated by the plasma. A method for reducing matrix interferences from a SCGD comprising introducing an internal standard into a sample to be analyzed, wherein the sample comprises at least one element of interest; determining a spatial emission profile of the internal standard; using linear correlation between the spatial emission profile of the internal standard and the element of interest to predict a crossover point; and using the (Continued)

crossover point of the element of interest to select a vertical acquisition height for SCGD analysis.

10 Claims, 15 Drawing Sheets

(51) Int. Cl.
*H05H 1/48* (2006.01)
*G01N 33/50* (2006.01)
*G01N 21/69* (2006.01)

(56) References Cited

U.S. PATENT DOCUMENTS

| | | | | |
|---|---|---|---|---|
| 6,815,369 | B2* | 11/2004 | Suzuki | H01J 37/32623 |
| | | | | 156/345.13 |
| 6,855,379 | B2* | 2/2005 | Jung | C23C 16/50 |
| | | | | 118/718 |
| 7,361,206 | B1* | 4/2008 | Jahn | B01D 53/268 |
| | | | | 73/23.37 |
| 7,929,138 | B1 | 4/2011 | Webb et al. | |
| 8,282,805 | B2* | 10/2012 | Daigle | B08B 7/0035 |
| | | | | 204/164 |
| 9,989,472 | B2* | 6/2018 | Schroeder | G01N 21/67 |
| 2005/0012038 | A1* | 1/2005 | Marcus | G01J 3/10 |
| | | | | 250/288 |

FOREIGN PATENT DOCUMENTS

| | | |
|---|---|---|
| CN | 104964966 A | 10/2015 |
| CN | 105004709 A | 10/2015 |

OTHER PUBLICATIONS

Zhenli Zhu, "Use of a Solution Cathode Glow Discharge for Cold Vapor Generation of Mercury with Determination by ICP-Atomic Emission Spectrometry", Anal. Chem. 2008 (Year: 2008).*

Krzysztof Greda, "Coupling of cold vapor generation with an atmospheric pressure glow microdischarge sustained between a miniature flow helium jet and a flowing liquid cathode for the determination of mercury by optical emission spectrometry", Anal. At. Spectrom., 2014 (Year: 2014).*

Lina Zheng and Pramod Kulkarni, "Rapid Elemental Analysis of Aerosols Using Atmospheric Glow Discharge Optical Emission Spectroscopy" Anal. Chem. May 17, 2017 (Year: 2017).*

Pal Mezei, "Pressure Dependence of the Atmospheric Electrolyte Cathode Glow Discharge Spectrum", Oct. 1997 (Year: 1997).*

Anqin Leng "Pump- and Valve-Free Flow Injection Capillary Liquid Electrode Discharge Optical Emission Spectrometry Coupled to a Droplet Array Platform", Dec. 1, 2016 (Year: 2016).*

International Patent Application No. PCT/CA2018/051249, International Search Report and Written Opinion dated Jan. 7, 2019.

Greda et al., "Reduction of Spectral Interferences in Atmospheric Pressure Glow Discharge Optical Emission Spectrometry," Microchemical Journal, Jan. 2017, vol. 130, pp. 7-13.

Park et al., "Fundamental Studies of Electrolyte-as-cathode Glow Discharge-atomic Emission Spectrometry for the Determination of Trace Metals in Flowing Water," Spectrochimica Acta Part B Atomic Spectroscopy, Jul. 1998, vol. 53 (6), pp. 1167-1179.

Schwartz et al., "Spatially Resolved Measurements to Improve Analytical Performance of Solution-Cathode Glow Discharge Optical-emission Spectrometry—Electronic Supplementary Information," Appendix A, Spectrochimica Acta Part B: Atomic Spectroscopy, Nov. 2016, vol. 125, pp. 168-176, Retrieved from [http://dx.doi.org/10.1016/j.sab.2016.10.004].

Schwartz et al., "Spatially Resolved Measurements to Improve Analytical Performance of Solution-Cathode Glow Discharge Optical-Emission Spectrometry," Spectrochimica Acta Part B: Atomic Spectroscopy, Nov. 2016, vol. 125, pp. 168-176.

Shirai et al., "Generation and Control of Electrolyte Cathode Atmospheric Glow Discharges using Miniature Gas Flow," Electrical Engineering in Japan, 2012, vol. 178 (4), pp. 269-274.

* cited by examiner

REDUCTION OF MOLECULAR BACKGROUND EMISSION AND SAMPLE MATRIX MANAGEMENT IN A SOLUTION CATHODE GLOW DISCHARGE

CROSS REFERENCE TO RELATED APPLICATIONS

This application claims the benefit of priority of U.S. Provisional Patent Application No. 62/567,278 filed Oct. 3, 2017, which is hereby incorporated by reference.

FIELD

The present disclosure relates generally to analysis by solution cathode glow discharge (SCGD). More particularly, the present disclosure relates to reduction of molecular background emission and to matrix management in SCGD.

BACKGROUND

Due to the inherent simplicity and operating characteristics of the solution cathode glow discharge (SCGD), it is emerging as a complimentary emission source to the well-known technique of inductively coupled plasma atomic emission spectrometry (ICP-AES).

Referring to FIG. 1A, a representation of a solution cathode glow discharge (SCGD) emission cell 10 found in the prior art is shown. A dc power source 20 connects to an anode 30 and a grounding electrode 40. The anode 30 may be, for example, a tungsten anode rod. The grounding electrode 40 may be, for example, a grounded graphite cathode rod. A capillary tube 50 delivers a solution sample 60 from a pump (not shown) proximate a top 70 of the grounding electrode 40. A plasma emission region 80 remains between an outlet tip 90 of the capillary tube 50 and a tip 100 of the anode 30. The capillary tube 50 may be, for example, a glass capillary tube. Upon activation of the power source 20, a plasma is formed in the plasma emission region 80.

The capillary tube 50 extends a distance (for example about 3 mm) above the top 70 of the grounding electrode 40, and the tip 100 of the anode 30 is a distance (for example about 3 mm) above the outlet tip 90 of the capillary tube 50. Electrical contact between the outlet tip 90 of the capillary tube 50 and the grounding electrode 40 is made along the vertical capillary tube 50 by the overflow of the solution sample 60 from the outlet tip 90 of the capillary tube 50. Optimized electrical contact between the outlet tip 90 of the capillary tube 50 and the grounding electrode 40 is made when the distance that the capillary tube 50 extends above the grounding electrode 40 is minimized. However, distances less than about 3 mm tend to promote a glow-to-arc transition where the plasma anchors to the grounding electrode 40 as opposed to the outlet tip 90 of the capillary tube 50. Electrical arcing can destroy electrode components and prohibits the analytical performance of the SCGD instrument. Therefore, typically a compromised distance of about 3 mm is used and 2.0 mL/min is the lowest flow rate for the solution sample 60 that can be used before analytical performance degrades.

Three different electrical resistance values are shown for a SCGD device found in the prior art. R1 is the ballast resistor 110 used to increase the output impedance of the dc power source 20 and limit the current delivered. R2 is the gas phase resistance of the plasma and R3 is the resistance of the electrical connection between the base of the plasma and the grounding electrode 40. This electrical connection is made through the overflow of the solution sample 60.

Referring to FIG. 1B, a prior art example of a SCGD apparatus is described in U.S. patent application Ser. No. 15/274,303 by Schroeder et al., published as US 2017/0097304, which is hereby incorporated by reference, discloses a SCGD device having a solution-catching collar, in the form of a weir 120.

SCGD may prove to be an excellent emission source for unattended operation for on-line analysis for industrial process control applications (on-line herein being real-time or near real-time collection or measurement or analysis of one or more process variables, such as analyte content or concentration or quantification thereof, to provide such information to a user and/or an industrial process control system). However, in many cases, the interfering emission spectra of atmospheric gases degrade the detection limits of this technique. K. Greda, P. Jamroz, and P. Pohl, "Atmospheric pressure glow discharge in a contact with liquid as a new excitation source in optical emission spectroscopy", Przemysl Chemiczny 91 (12) (2012) 2389-2397, which is hereby incorporated by reference, shows the background emission spectrum of the SCGD. Other than the OH background emission that originates from the aqueous sample solution, all dominant interfering background features originate from atmospheric gases.

Previous attempts at reducing the presence of molecular background emission have included purging the plasma cell with an inert gas and adding chemical modifiers to the sample solution (the plasma cell being at least the portion of the SCGD emission cell 10 proximate the anode 30 and the solution sample 60, including the plasma emission region 80), each of the following is hereby incorporated by reference:

Y. S. Park, S. H. Ku, S. H. Hong, H. J. Kim and E. H. Piepmeier, "Fundamental studies of electrolyte-as-cathode glow discharge-atomic emission spectrometry for the determination of trace metals in flowing water", Spectrochimica Acta Part B, 1998, 53, 1167-1179.

G. Jenkins, J. Franzke and A. Manz, "Direct optical emission spectroscopy of liquid analytes using an electrolyte as a cathode discharge source (ELCAD) integrated on a micro-fluidic chip", Lab Chip, 2005, 5, 711-718.

N. Shirai, M. Nakazawa, S. Ibuka and S. Ishii, "Generation and Control of Electrolyte Cathode Atmospheric Glow Discharge Using Miniature Gas Flow", Electrical Engineering in Japan, 2012, 178, 269-274.

K. Greda, K. Swiderski, P. Jamroz and P. Pohl, "Reduction of spectral interferences in atmospheric pressure glow discharge optical emission spectrometry", Microchemical Journal, 2017, 130, 7-13.

K. Greda, P. Jamroz and P. Pohl, "Effect of the addition of non-ionic surfactants on the emission characteristic of direct current atmospheric pressure glow discharge generated in contact with a flowing liquid cathode", J. Anal. At. Spectrom., 2013, 28, 134-141.

K. Greda, P. Jamroz and P. Pohl, "The improvement of the analytical performance of direct current atmospheric pressure glow discharge generated in contact with the small-sized liquid cathode after the addition of non-ionic surfactants to electrolyte solutions", Talanta, 2013, 108, 74-82.

T. A. Doroski and M. R. Webb, "Signal enhancement in solution-cathode glow discharge—optical emission spectrometry via low molecular weight organic compounds", Spectrochimica Acta Part B, 2013, 88, 40-45.

Although purging the plasma cell with an inert gas is a technique that can be used to reduce interfering molecular emission, the need to replace gas cylinders would hinder the SCGD from being used in an unattended on-line environment.

China patent CN 104964966(A) "Integrated atomic spectrum atomizer" describes a SCGD apparatus with a closed shell around the anode and cathode, which prevents entry of external airflow; however, the system is fully sealed to the atmosphere, making maintenance and replacement of components difficult.

There is a need in the art for a simple method of reducing molecular background emission that is suitable for an on-line, industrial environment.

SCGD instrument performance can also be significantly degraded by sample matrix interferences. For example, the atomic emission signal can be attenuated when significant components of phosphate or sodium are present in the sample matrix. A. J. Schwartz, S. J. Ray, G. C. Y. Chan and G. M. Hieftje, "Spatially resolved measurements to improve analytical performance of solution-cathode glow discharge optical-emission spectrometry", *Spectrochimica Acta Part B*, 2016, 125, 168-176. (including Electronic Supplementary Information referenced therein), hereby incorporated by reference, and herein referred to as Schwartz (2016) has recently shown how an imaging spectrograph can be used to record the spatially resolved emission spectra from a SCGD. Schwartz (2016) has observed that locations exist along the vertical profile of the discharge where matrix interference is reduced and even eliminated. The so-called crossover point is the location where sample matrix interferences go to zero. Ideally, acquisition parameters (i.e. the observation height) should be made around this crossover point. Determining this crossover point in a reliable manner is only possible when atomic emission signals are acquired that are free from interfering noise. Schwartz (2016) accomplished a high signal-to-noise ratio acquisition by using a calcium concentration of 20 ppm. However, determining the crossover point for calcium at 1.0 ppb (20,000 times lower) would require the elimination of interfering molecular emission.

The use of a purged configuration to eliminate atmospheric gases from the plasma region would allow the use of crossover points to manage matrix interferences when analyte concentrations are very low.

SUMMARY

The present disclosure provides a device and method for purging atmospheric gases from a solution cathode glow discharge (SCGD).

The presently disclosed apparatus and methods are applicable to SCGD, including the generic SCGD of FIG. 1A and the Schroeder et al. SCGD of FIG. 1B and otherwise.

In a first aspect the present disclosure provides a purging device for purging atmospheric gases from a solution cathode glow discharge (SCGD) apparatus, comprising a hollow body that encloses a plasma generated between a solid anode and a solution cathode, wherein the body comprises at least one opening for release of water vapor generated by the plasma.

In an embodiment disclosed, the body comprises a cylinder.

In an embodiment disclosed, the body has a sealed top and an open bottom.

In an embodiment disclosed, the body has a sealed top and a sealed bottom.

In an embodiment disclosed, the opening comprises one or more slots in a wall of the body.

In an embodiment disclosed, the one or more slots are adapted to allow visual observation and detection of emitted light from the SCGD.

In an embodiment disclosed, the body is a stainless steel tube.

In an embodiment disclosed, the sealed top comprises a plurality of pieces.

In an embodiment disclosed, the sealed top comprises an upper piece and a lower piece, the lower piece having a larger internal diameter than the upper piece.

In a further aspect, the present disclosure provides a SCGD apparatus including a purging device as provided by the present disclosure.

In a further aspect, the present disclosure provides method for reducing matrix interference in a SCGD analysis of a sample to be analyzed, wherein the sample comprises at least one element of interest, the method includes a. determining a spatial emission profile of an internal standard, b. determining a spatial emission profile of the at least one element of interest, c. determining a linear correlation between the spatial emission profile of the internal standard and the spatial emission profile of the at least one element of interest, d. introducing the internal standard into the sample, e. using SCGD analysis of the sample, measure a crossover point of the internal standard, and f. selecting a vertical acquisition height for SCGD analysis of the sample for the at least one element of interest from the crossover point of the internal standard using the linear correlation.

In an embodiment disclosed, the method further includes g. obtaining a SCGD analysis of the sample, centered at about the vertical acquisition height, and h. measuring the emission intensity of the at least one element of interest to provide the SCGD analysis of the sample.

In an embodiment disclosed, a. to c. are performed in advance, in a calibration portion of the method and d. to h. are performed subsequently, repeatedly, continuously or semi-continuously in a measurement portion of the method.

In an embodiment disclosed, the sample comprises a variable matrix, wherein the spatial emission profile of the internal standard in a. and the spatial emission profile of the at least one element of interest in b. are determined for a plurality of conditions of the variable matrix, wherein the crossover point in e. is a matrix-free crossover point, independent of the variable matrix, and wherein the crossover point in f. is the matrix-free crossover point.

In an embodiment disclosed, the variable matrix comprises variable sodium (Na) concentration.

In an embodiment disclosed, the internal standard or the at least one element of interest or both comprise an alkali-metal cation.

In an embodiment disclosed, the internal standard comprises Ga and is substantially free of Ca and Mg, and wherein the at least one element of interest comprises Ca or Mg or both.

In an embodiment disclosed, the sample comprises boiler feedwater. In an embodiment disclosed, the method further comprises determining a water hardness of the boiler feedwater from a concentration of Ca or Mg or both.

In an embodiment disclosed, the method further includes providing a SCGD apparatus as described herein, wherein the SCGD analysis is performed using the SCGD apparatus.

DETAILED DESCRIPTION

Figure 1A:
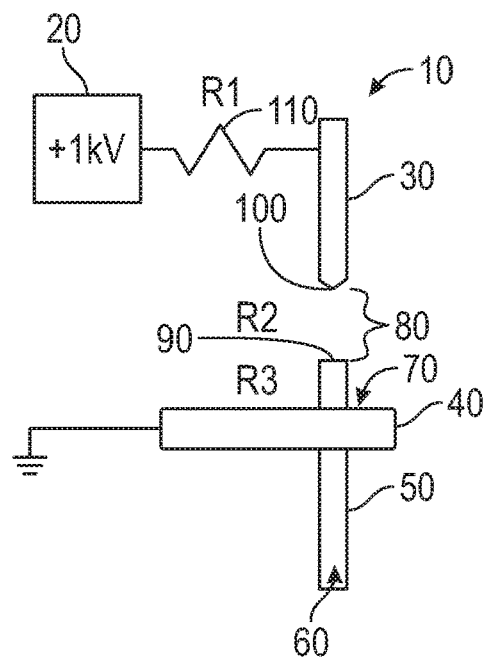
FIG. 1A is a prior art SCGD without a purging device of the present disclosure.
Figure 1B:
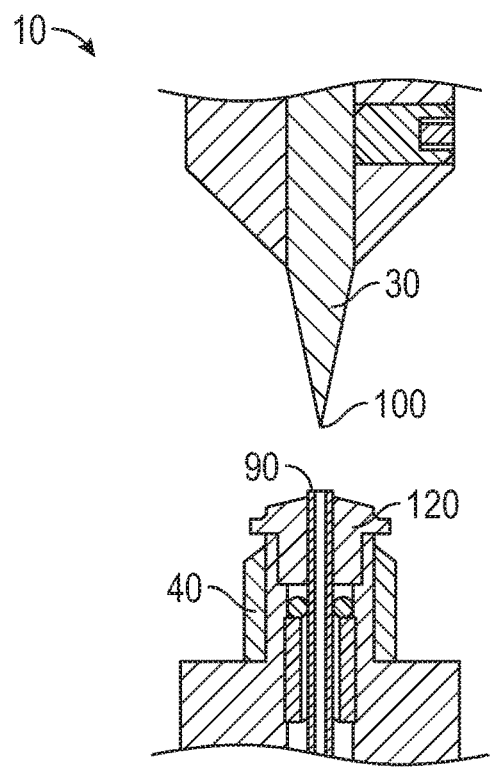
FIG. 1B is a SCGD without a purging device of the present disclosure.
Figure 1C:
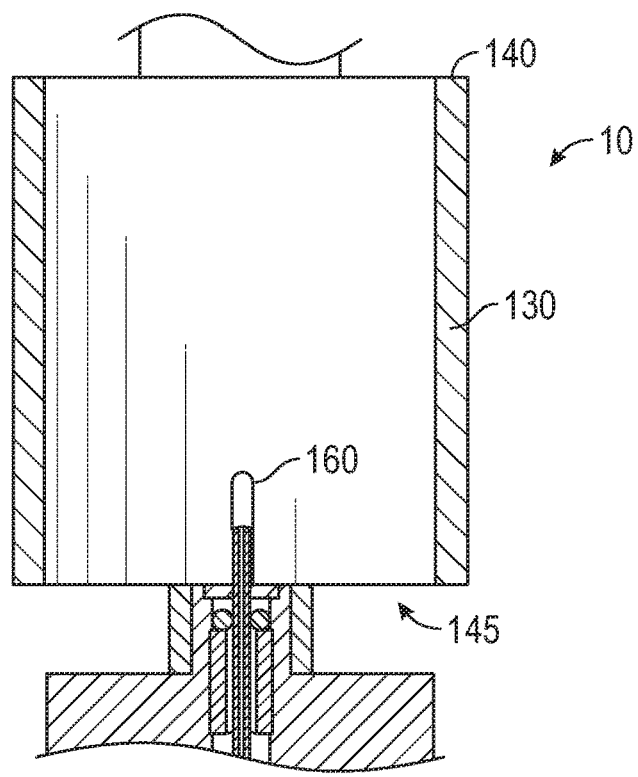
FIGS. 1C-1D depict an example of a solution cathode glow discharge with a purging device with a sealed top and open bottom.
Figure 1D:
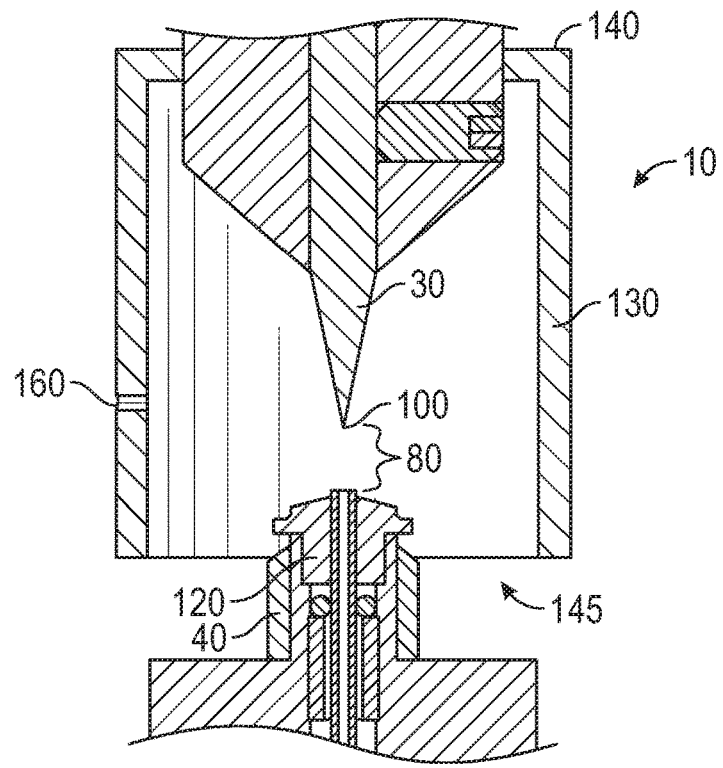

In a first embodiment, referring to FIGS. 1C-1D, a purging device, shown in the form of a tube 130 having an open bottom 145 is provided for the SCGD emission cell 10. The tube 130 may be for example a stainless steel tube (O.D. 19 mm or 0.75"). The tube 130 is sealed on the top 140 so that all the water vapor produced by the plasma must exit either through the bottom 150 or through an aperture, shown in the form of a small slot 160 facing the spectrometer (not shown). Slot 160 and the spectrometer entrance slit (not shown) are aligned. FIG. 1C shows the outside of the purging device around the SCGD; FIG. 1D shows a cross-section of the same. In an embodiment disclosed, the O.D. of the tube is 19 mm and the remainder of the figure is drawn approximately to scale. In FIG. 1D, the purging device has been rotated by 90 degrees with respect to the purging device in FIG. 1C, e.g. clockwise if viewed from above.

In an embodiment disclosed, the tube 130 is electrically isolated from the anode and ground. In an embodiment disclosed, the tube 130 is brought to ground potential.

A significant proportion of the water pumped to the SCGD is vaporized when it interacts with the high temperature plasma. When this water vapor is contained by the tube 130, it purges the plasma emission region 80 of atmospheric gases such as nitrogen, oxygen, and carbon dioxide. Background emission from atmospheric gases is thus eliminated or at least reduced from the spectra produced by the SCGD and the elimination or reduction of this background emission significantly improves the signal-to-noise ratio of this analytical technique.

Additionally, the full viewing height between the tip 100 of the anode 30 and the flowing solution sample 60 (cathode) can now be used since the interfering molecular emission near the anode 30 has been eliminated. Taking advantage of the full viewing height of the plasma emission region 80 will allow for the effective management of matrix interferences per the method described below.

In a second embodiment, referring to FIGS. 2A-2E, the tube 130 is sealed on the top 140 and the bottom 150 so that all the water vapor produced by the plasma must exit through a plurality of apertures, two slots 170 and 180 shown. The stainless steel tube has two slots to allow visual observation and detection of emitted light. In an embodiment disclosed, the O.D. of the tube is 1.75" and the remainder of the figure is drawn approximately to scale.

The top 140 and the bottom 150 may be made from machinable non-porous ceramic (e.g. Macor™), which is an electrical insulator. The top 140 may be made from a plurality of pieces (two shown). An upper piece 142 of the top 140 has a smaller internal diameter than the lower piece 144. The upper piece 142 fits snuggly around the anode 30 and rests atop the lower piece 144 (but is not affixed to the lower piece 144). The lower piece 144 has a larger internal diameter and provides a gap 146, e.g. an annular gap, between the internal diameter of the lower piece 144 and the anode 30 (see FIG. 2D). The gap 146 allows the anode 30 and associated anode assembly to be shifted horizontally to align the anode tip 100 with the capillary tube 50, while maintaining a seal between the upper piece 142 and the lower piece 144. The snug-fitting upper piece 142 rests on top of the lower piece 144 to prevent water vapor from escaping through the gap in the lower piece 144. In an embodiment disclosed, a floating seal is formed between the upper piece 142 and the lower piece 144, which allows relative horizontal movement between the upper piece 142 and the lower piece 144.

A drain 190 (FIG. 2B) through the bottom 150 to allow the waste sample solution to drain from the plasma cell. A drain tube (not shown) is connected to the drain 190 that directs the waste sample solution to a waste reservoir (not shown). The bottom of the drain tube is submersed in waste sample solution in the waste reservoir. This forces all of the water vapor from the plasma-water interaction to exit through the slots 170 and 180.

The slots 170 and 180 allow detection of emitted light and visual observation respectively. The tube 130 of the second embodiment (FIGS. 2A-2E) is also larger than the tube 130 of the first embodiment (FIGS. 1C-1D), for example with an O.D. of 1.75". The second embodiment provided complete purging of atmospheric gases as in the first embodiment.

Figure 2B:
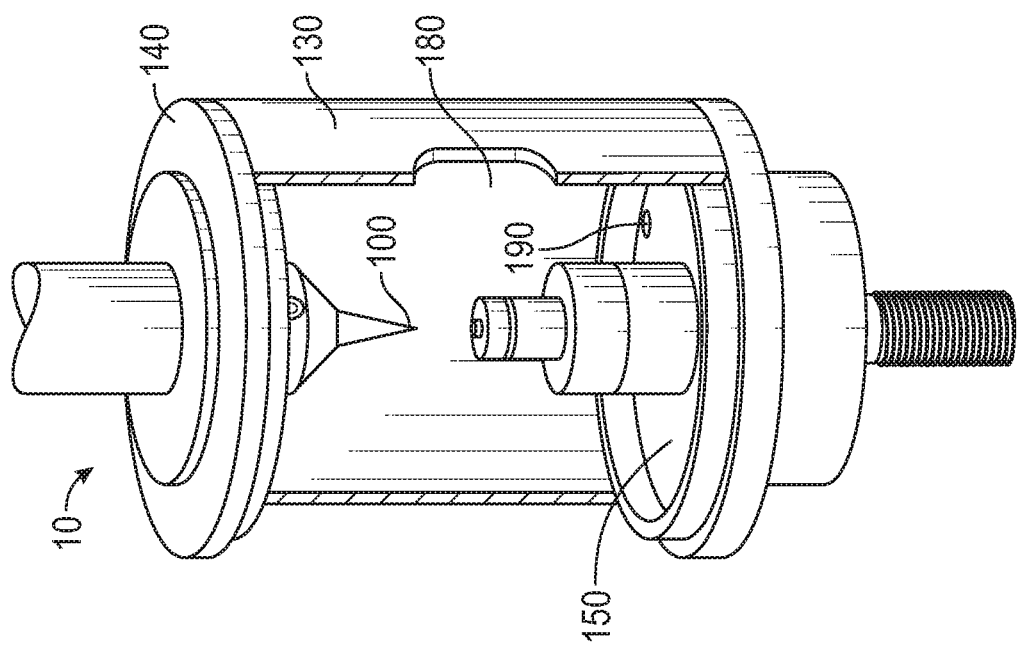
FIGS. 2A-2E depict an example of a solution cathode glow discharge with a purging device with a sealed top and bottom.
Figure 2A:
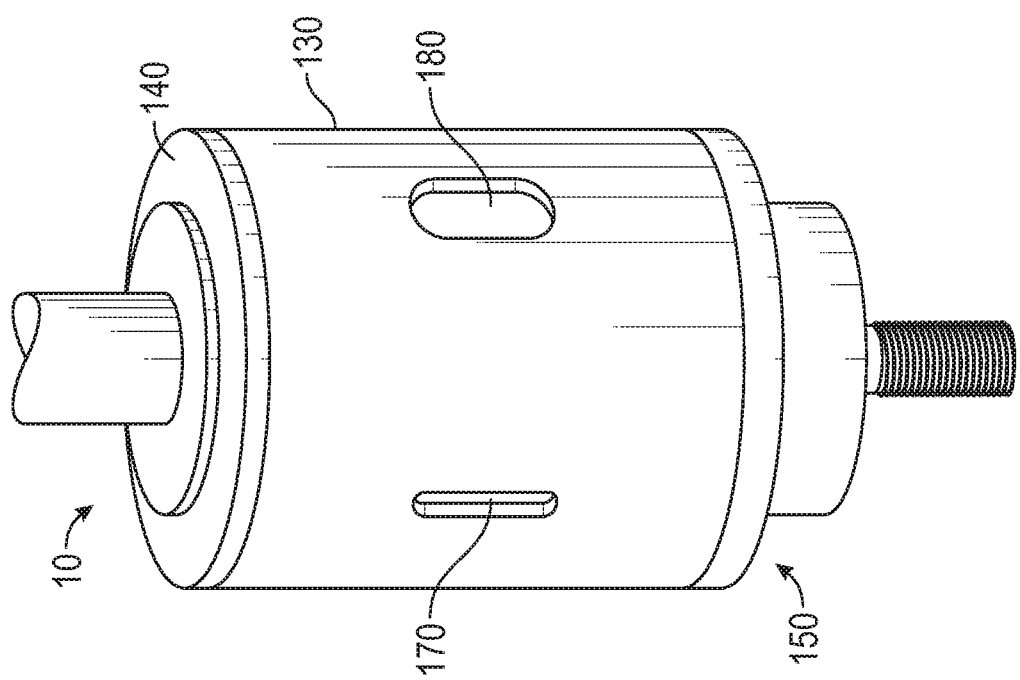
Figure 2D:
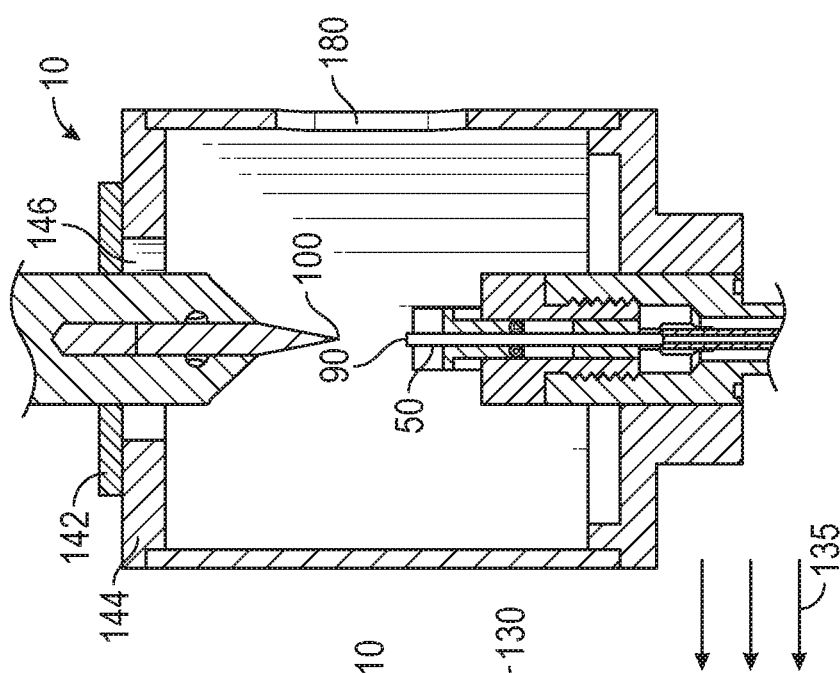
Figure 2E:
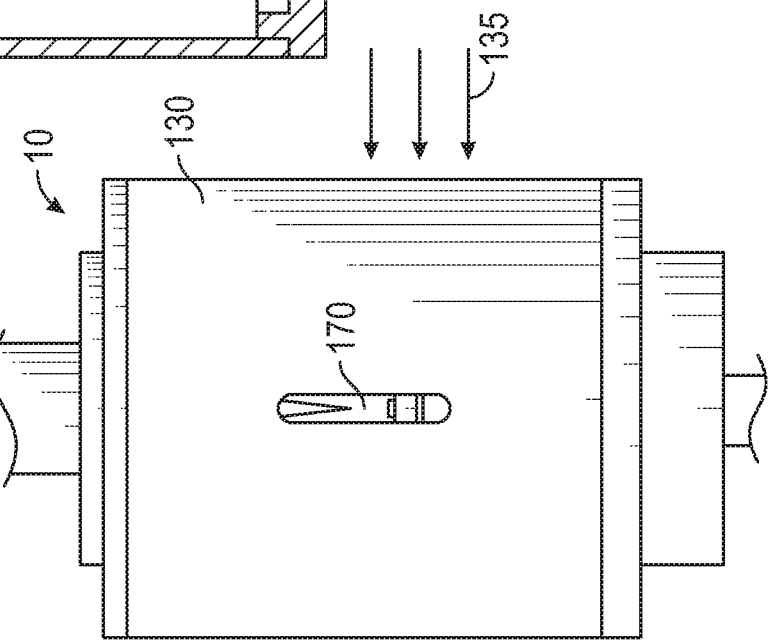
Figure 2C:
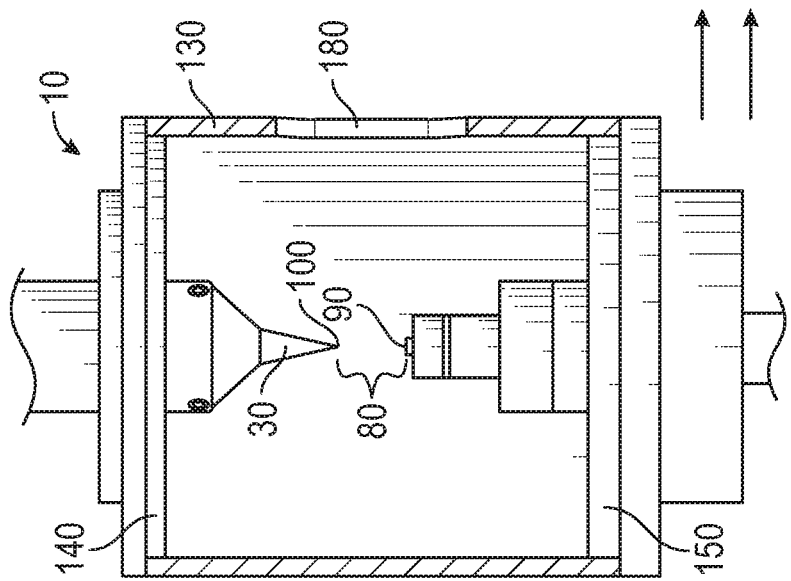

Slot 170 is narrower than slot 180. It is narrower to aid in blocking random droplets from the plasma impinging on an external optical window (not shown). The slot 170 and the slot 180 are offset by an angular offset (for example about 90 degrees as shown in FIG. 2A). Slot 170 and the spectrometer entrance slit (not shown) are aligned, and the slot 180 may be used for visual observation by an operator while the spectrometer is used to measure the emission spectra via the slot 170. The dimensions of the slots 170 and/or 180 are chosen so that they are small enough to effectively block atmospheric gases (e.g. nitrogen) from entering the plasma cell and large enough to minimize the effort required for optical alignment.

In an embodiment disclosed, the tube 130 is electrically isolated from the anode and ground. The tube 130 may pick up a charge from the plasma, but this floating potential is assumed to be negligible. In an embodiment disclosed, the tube 130 is brought to ground potential. In an embodiment disclosed, a larger sized body for the purging device, e.g. larger diameter tube 130 is selected to reduce the risk of the plasma arcing to the tube 130 from the tip 100 of the anode 30 and to provide a larger volume of the plasma cell that reduces the risk of the sample boiling inside the cell.

Adding the purging device, e.g. tube 130 may create a potential concern of trapping too much heat from the plasma that may lead to temperatures that exceed the boiling point of the waste sample solution. Violent boiling of the waste sample solution is not desired since it would contribute to plasma instability. Such boiling was not observed for the tube 130 having an open bottom 145 (first embodiment, FIGS. 1C-1D) nor for the tube 130 having a sealed bottom 150 (second embodiment, FIGS. 2A-2E), but the diameter (and thus internal volume and surface area) was increased for the second embodiment to reduce a concern for elevated temperatures that may lead to undesired boiling of the waste sample solution. With a higher volume inside the stainless steel tube 130 and a higher surface area of the tube 130 that assists cooling, elevated temperatures that lead to boiling of the waste solution have not been observed. In an embodiment disclosed, external cooling may be applied to the tube 130, for example by supplying an air flow 135 (see FIG. 2E) of a few litres per minute directed at the outside of the stainless steel tube 130 to remove some excess heat. A larger stainless steel tube 130 was also used in the second embodiment (FIGS. 2A-2E) to reduce or eliminate the likelihood of electrical arcing to the tube from the high voltage applied to the anode 30.

While FIGS. 1C-1D and 2A-2E depict a generally uniform cylindrical/tubular purging device, the purging device may be configured in a different shape or manner or both. For example, in an embodiment disclosed, the purging device may be rectangular, cube shaped, etc. In an embodiment disclosed, the purging device is a hollow body that at least partially encloses the plasma cell, while providing controlled exit of water vapor from the plasma cell and permitting observation of the plasma emission region 80 by a spectrometer (not shown).

As shown in the examples below, the inclusion of a purging device to a SCGD apparatus substantially eliminates the interfering molecular emission for the analysis of calcium and gallium. In addition, lower detection limits were achieved for a variety of elements commonly analyzed by SCGD, demonstrating an improved signal-to-noise ratio.

The present disclosure also provides a unique method of reducing matrix interferences in SCGD analyses using the correlation between spatial emission profiles from one element to another.

As described in Schwartz (2016), there exists a location in the vertical profile of the plasma where matrix interferences are substantially eliminated if emission is measured from that location (i.e. the crossover point). As shown in the present disclosure, the inventors have found that spatial analysis can be performed on one internal standard, spiked at a high concentration, and the appropriate crossover points of other elements can be determined by a correlation function (rather than performing spatial analysis of each element individually). By eliminating molecular background emission, the purging device of the present disclosure allows the use of crossover points to manage matrix interferences when analyte concentrations are very low. Theoretically any element can be used as an internal standard. In some embodiments, the internal standard is gallium.

Example 1

Purging Device

Figure 3A:
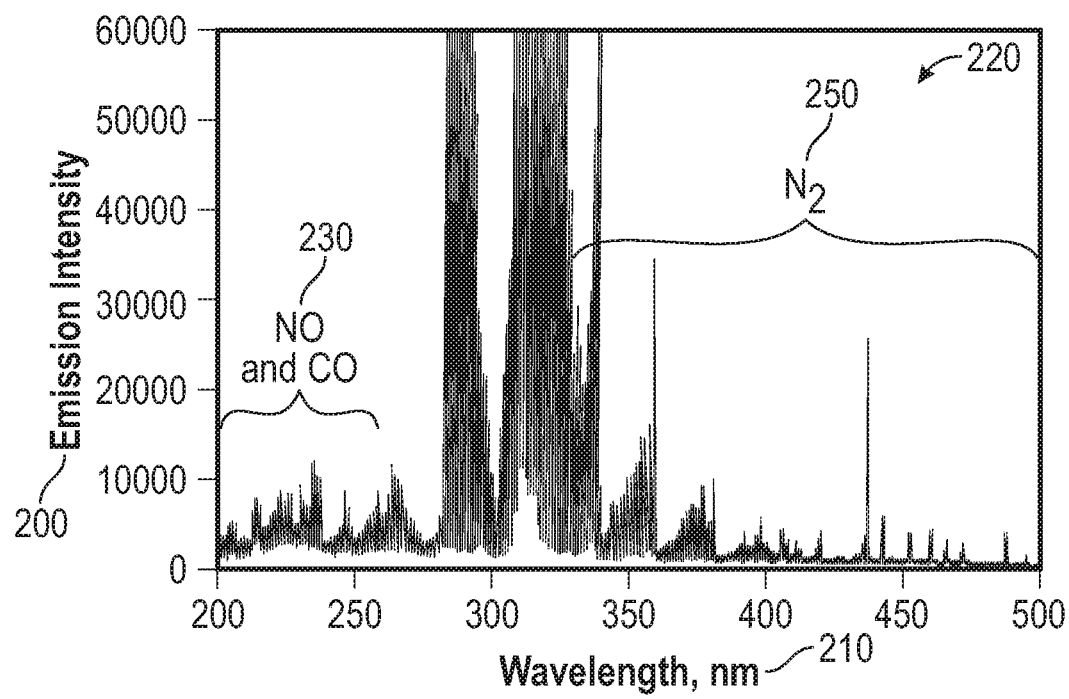
FIGS. 3A-3B depict a comparison of the background emission spectra without (3A) and with (3B) atmospheric gas purging.
Figure 3B:
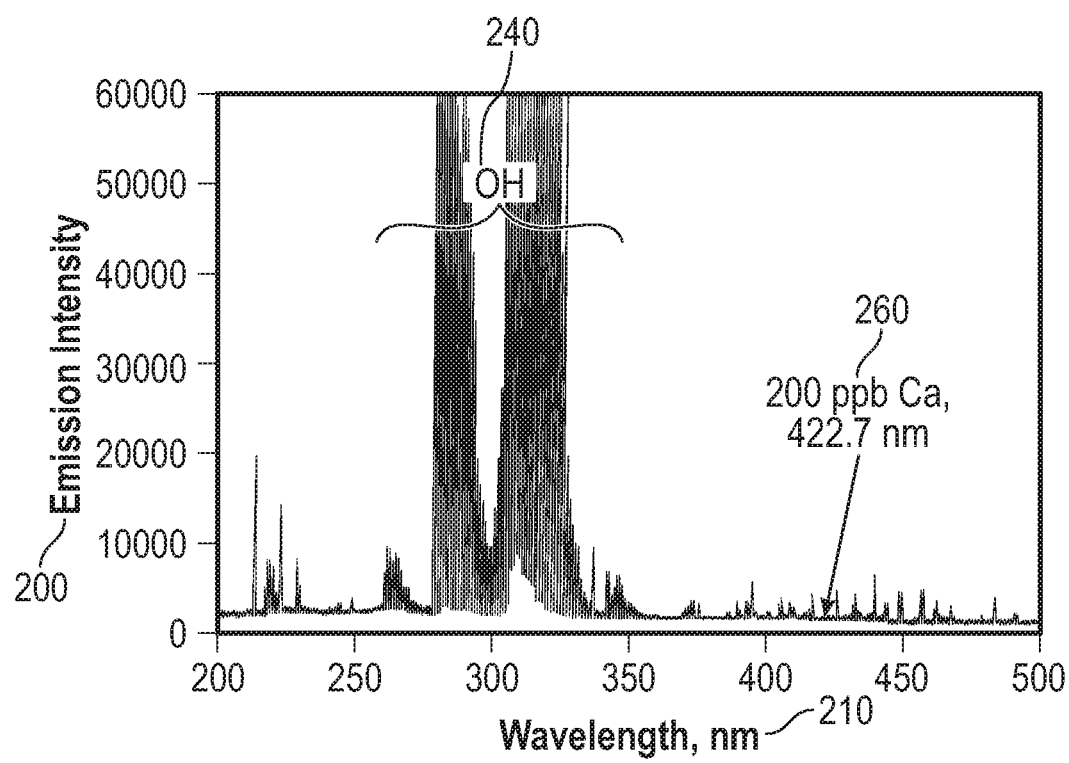
Figure 4A:
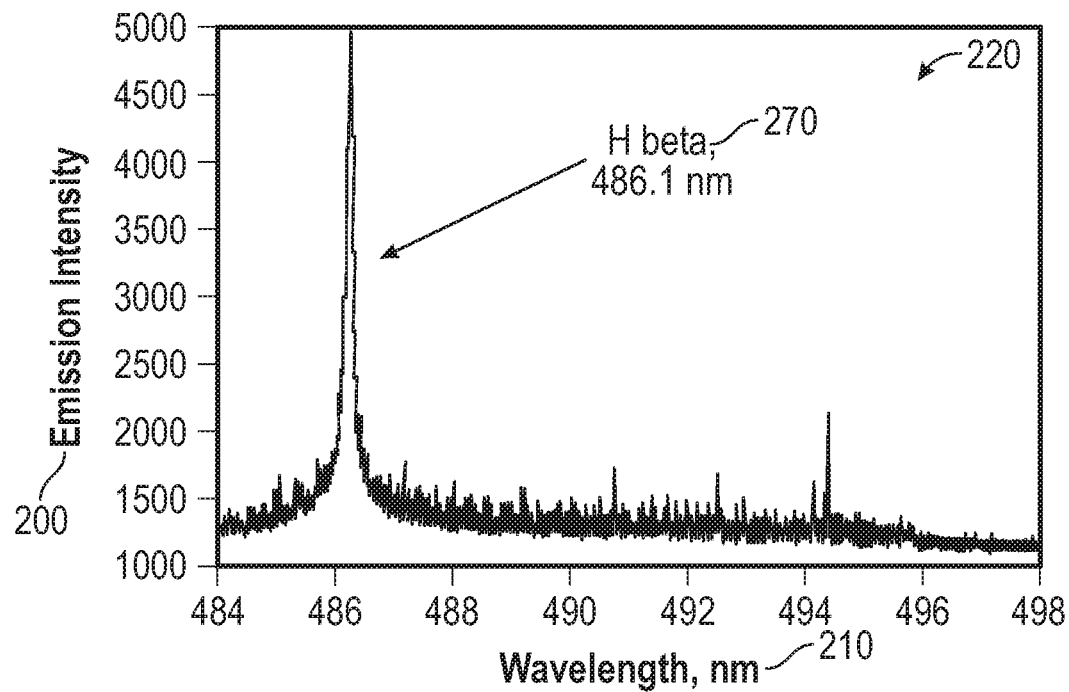
FIG. 4A-4B depict a comparison of the background emission spectra without (4A) and with (4B) atmospheric gas purging.
Figure 4B:
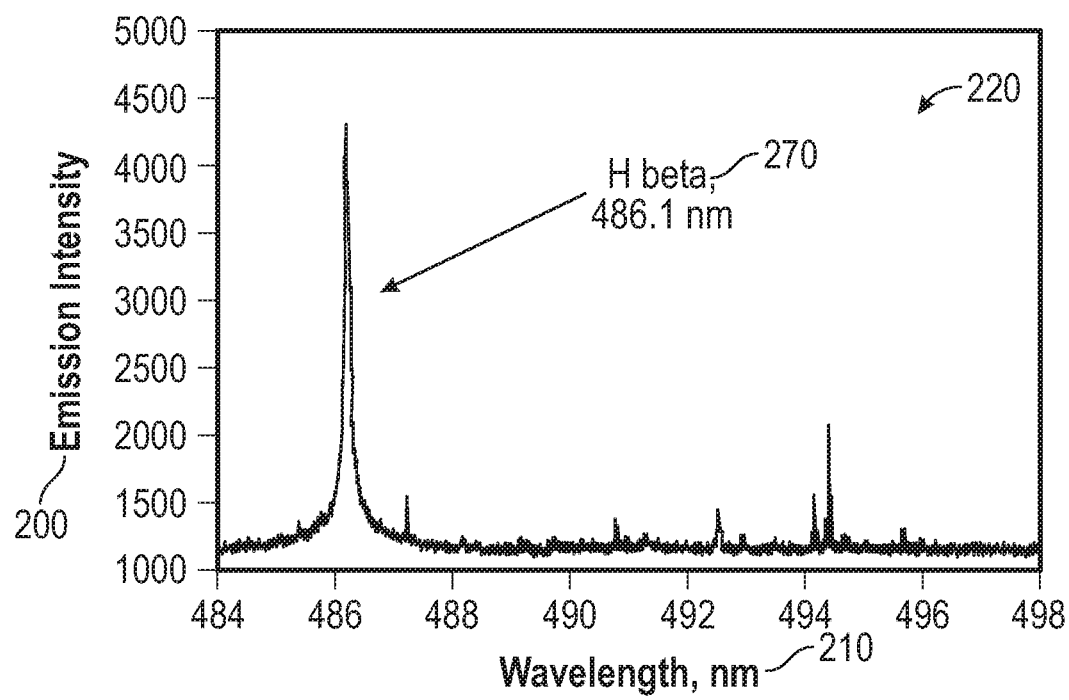

Experiments were performed using a purging device with an O.D. of 19 mm and the open bottom tube design as illustrated in FIGS. 1C-1D. The background emission spectra and atomic emission for an unpurged and purged SCGD is shown in FIG. 3A and FIG. 3B, respectively, showing emission intensity 200 versus wavelength 210 in nm for the spectra 220. These spectra 220 originate from the same solution sample and were acquired with the same acquisition parameters. Identical acquisition parameters were used for both spectra including 80 mA current, 0.1 s integration, full vertical pixel usage (1-512), 30 micron spectrometer entrance slit, 1.0 mL/min sample flow rate, and 0.1M $HNO_3$ spiked at 200 ppb with a 23 element standard solution (FIGS. 3A/3B and FIGS. 4A/4B). The sample solution contains 200 ppb of Ag, Al, B, Ba, Bi, Ca, Cd, Co, Cr, Cu, Fe, Ga, In, K, Li, Mg, Mn, Na, Ni, Pb, Sr, Tl, and Zn. Molecular background emission from NO, CO, (see e.g. FIG. 3A NO and CO (230)), OH (240), and $N_2$ (250) is clearly visible. Narrow line-width atomic emission is easier to observe in the purged configuration between 200-250 nm and 365-500 nm. The purged configuration cannot remove the presence of OH bandhead emission seen between 255 and 355 nm. However, this OH emission can be managed with adequate optical resolution for the determination of Mg at 285.2 nm and Cu at 327.4 nm. Although not clearly visible in FIG. 3A, the $N_2$ background emission extends all the way to 500 nm as seen in FIG. 4A (without purging) and FIG. 4B (with purging). With a 0.1 s integration time, the detection of Ca becomes observable in FIG. 3B (200 ppb Ca, 422.7 nm (260)). The spectra 220 also indicates H beta, 486.1 nm (270).

Figure 5A:
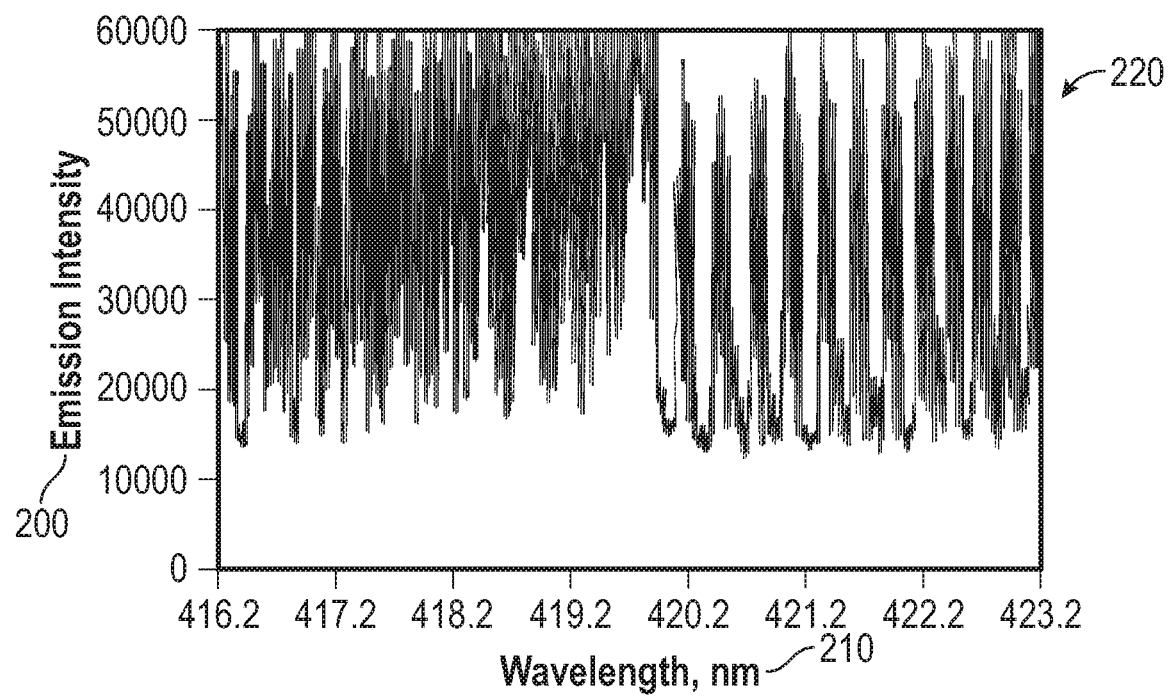
FIGS. 5A-5B depict a comparison of the background emission spectra without (5A) and with (5B) atmospheric gas purging.
Figure 5B:
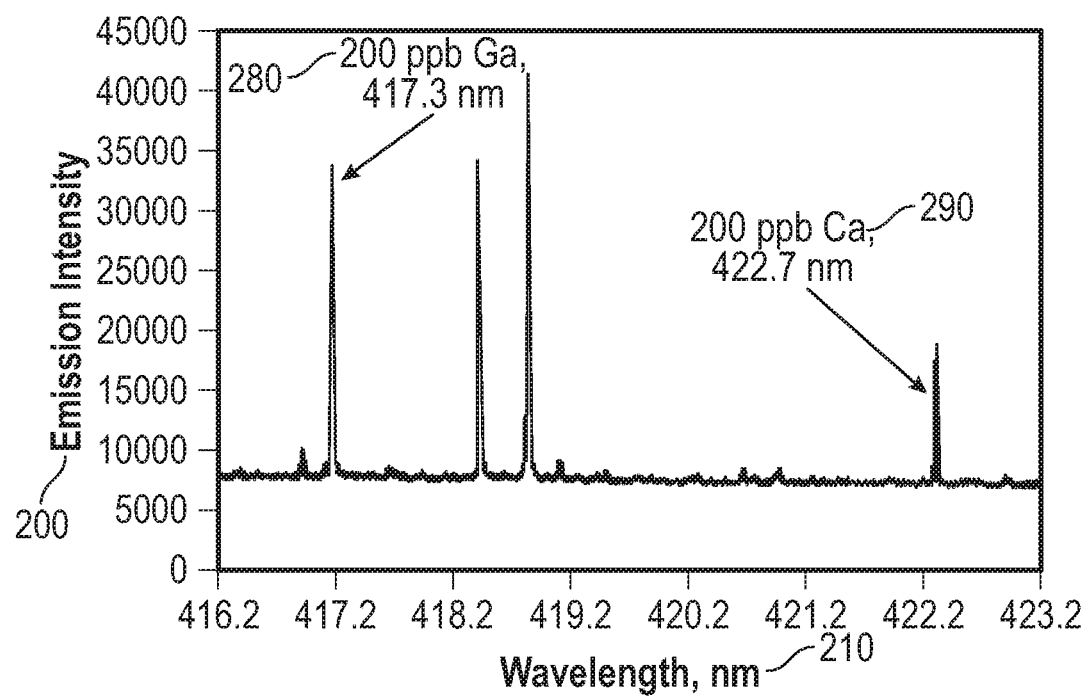

The usefulness of purging atmospheric gases from the plasma region is dramatically illustrated in FIG. 5A/5B for the detection of calcium (Ca) and gallium (Ga) where a 5 s integration time is used. Identical sample and acquisition parameters are used for FIGS. 5A and 5B. Identical acquisition parameters were used for both spectra including 80 mA current, 5 s integration, full vertical pixel usage (1-512), 30 micron spectrometer entrance slit, 1.0 mL/min sample flow rate, and 0.1M $HNO_3$ spiked at 200 ppb with a 23 element standard solution. In the unpurged configuration (FIG. 5A), the emission of calcium is superimposed on top of the emission of $N_2$. Therefore, any fluctuation or noise in the $N_2$ spectrum will be added to the noise for calcium and gallium and detecting Ca or Ga in the resulting spectra 220 is difficult if not impossible. The magnitude of the $N_2$ interference for calcium and gallium is relatively small as observed in FIG. 3A and 200 ppb Ga, 417.3 nm (280) and 200 ppb Ca, 422.7 nm (290) are readily detectable in FIG. 5B. For other regions of the spectrum where interfering molecular emission is more pronounced, the improvement in the signal to noise ratio will be even greater than what is displayed in FIG. 5B.

Figure 6A:
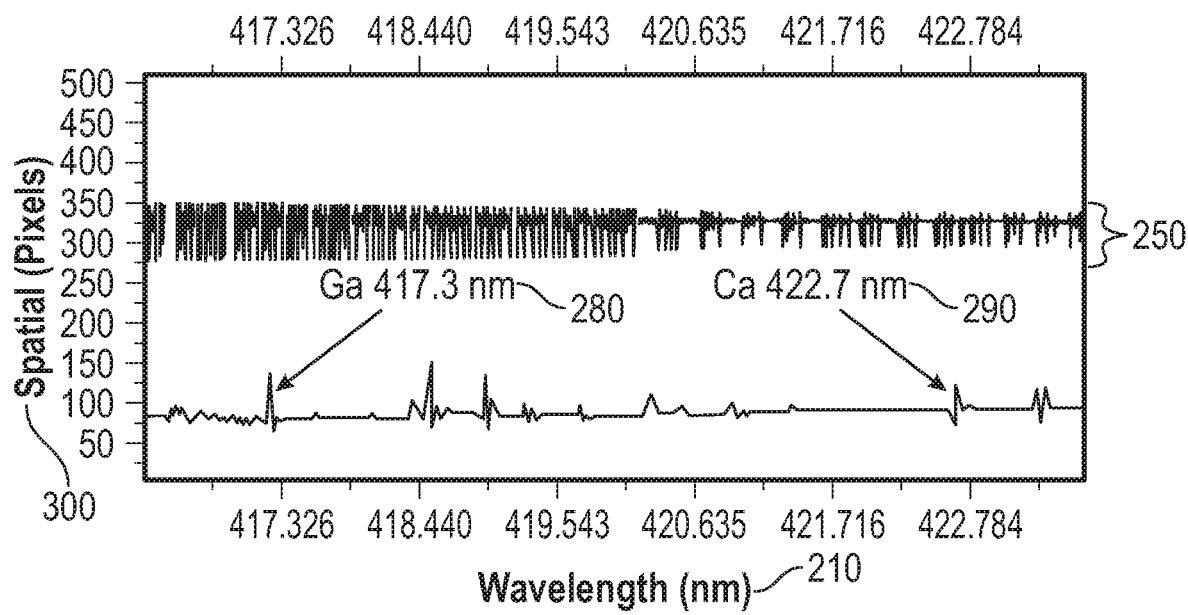
FIGS. 6A-6B depict a comparison of the background emission spectra without (6A) and with (6B) atmospheric gas purging.
Figure 6B:
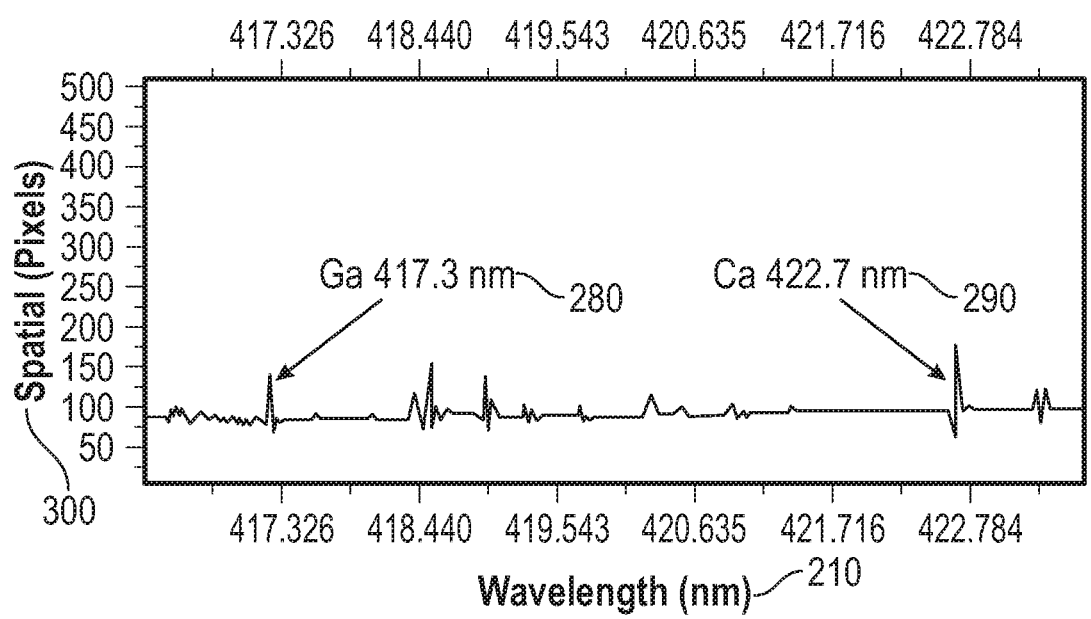

When using a two dimensional array detector, e.g. charged coupled device (CCD), it is possible to record an image of the plasma and obtain spatial information regarding plasma emission. This is illustrated in FIGS. 6A/6B where identical sample solution and acquisition parameters are used with an unpurged (FIG. 6A) and purged (FIG. 6B) configuration. Image analysis of the SCGD was performed as illustrated in Schwartz (2016). Identical acquisition parameters were used for both spectra including 80 mA current, 200 s integration, full vertical pixel usage (1-512), 30 micron spectrometer entrance slit, 1.0 mL/min sample flow rate, and 0.1M $HNO_3$ spiked at 200 ppb with a 23 element standard solution. Vertical pixel number, spatial (pixels) (300) is plotted against wavelength and the vertical pixel number correlates to the location between the 3 mm electrode gap where emission occurs (e.g. the plasma emission region 80 between the outlet tip 90 of capillary tube 50 and tip 100 of anode 30, see FIG. 2C). The emission from calcium at 422.7 nm and gallium at 417.3 nm respectively is seen to be most prominent near the cathode but also to fill the 3 mm gap towards the anode. FIG. 6B is a spatial emission image analysis showing Ga emission at 417.3 nm and Ca emission at 422.7 nm. What is most observant from FIG. 6B is the complete absence of $N_2$ molecular emission in the purged configuration in contrast to the molecular emission lines (dark features near the top of FIG. 6A, marked 250).

Eliminating background emissions using the purging device of the present disclosure was found to substantially lower detection limits in multiple elements of interest to SCGD analyses as shown in Table 1. The detection limits were calculated as three times the standard deviation of the blank signal divided by the slope of the calibration curve ($3\sigma_{blk}$/slope). The standard deviation of the blank signal was calculated based on 16 consecutive readings.

TABLE 1

| Element | Detection Limit (ppb or ng/mL) |
|---|---|
| Ni | 0.6 |
| Co | 2 |
| Zn | 0.5 |
| Ca | 0.4 |
| Mg | 0.02 |
| In | 0.08 |
| Ga | 0.2 |
| Tl | 0.08 |
| Al | 7 |
| Na | 0.003 |

Example 2

Sample Matrix Management

The following experimental conditions were used in this Example:

| | |
|---|---|
| SCGD current | 80 mA |
| Ballast resistor | 25 kΩ |
| Slit width | 30 μm for Ca and Ga, and Mg |
| Amplification setting | high sensitivity, for Ca and Ga; high light for Mg |
| Sample flow rate | 1.0 mL/min |
| Standard Concentrations | 200 ppb for Mg, Ga, and Ca |
| Matrix | 0.1M $HNO_3$, sodium ranging from 0 to 500 ppm |
| Image Analysis | 230 s integration for Ca and Ga, 60 s integration for Mg |
| Magnesium | 285.2 nm (see FIGS. 9 and 12) |
| Calcium | 422.7 nm |
| Gallium | 417.3 nm |
| Interference filter | 320 nm filter used for Ca and Ga |

Figure 7:
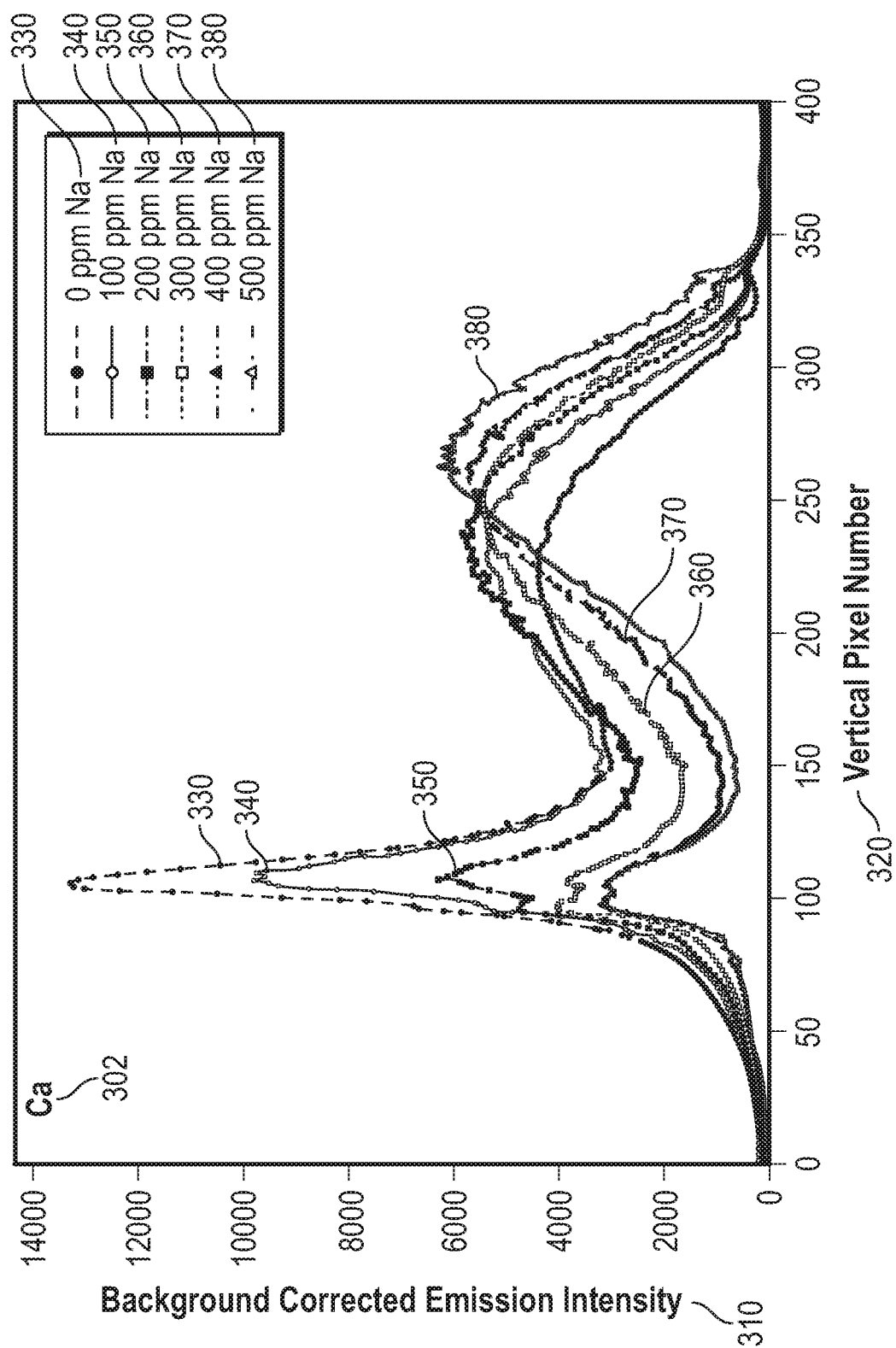
FIG. 7 depicts the 200 ppb Ca spatial emission profile with different sodium concentrations.
Figure 8:
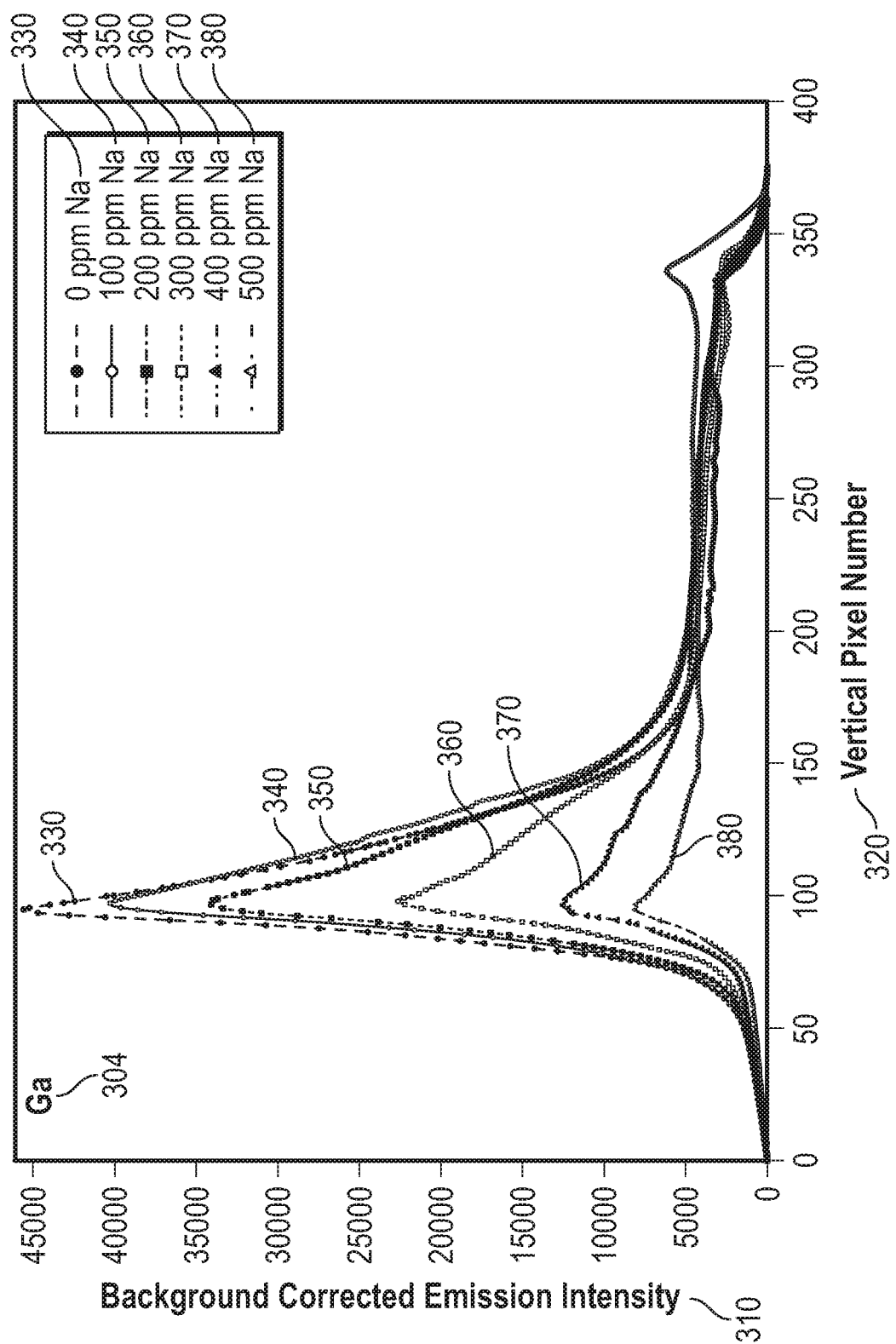
FIG. 8 depicts the 200 ppm Ga spatial emission profile with different sodium concentrations.
Figure 9:
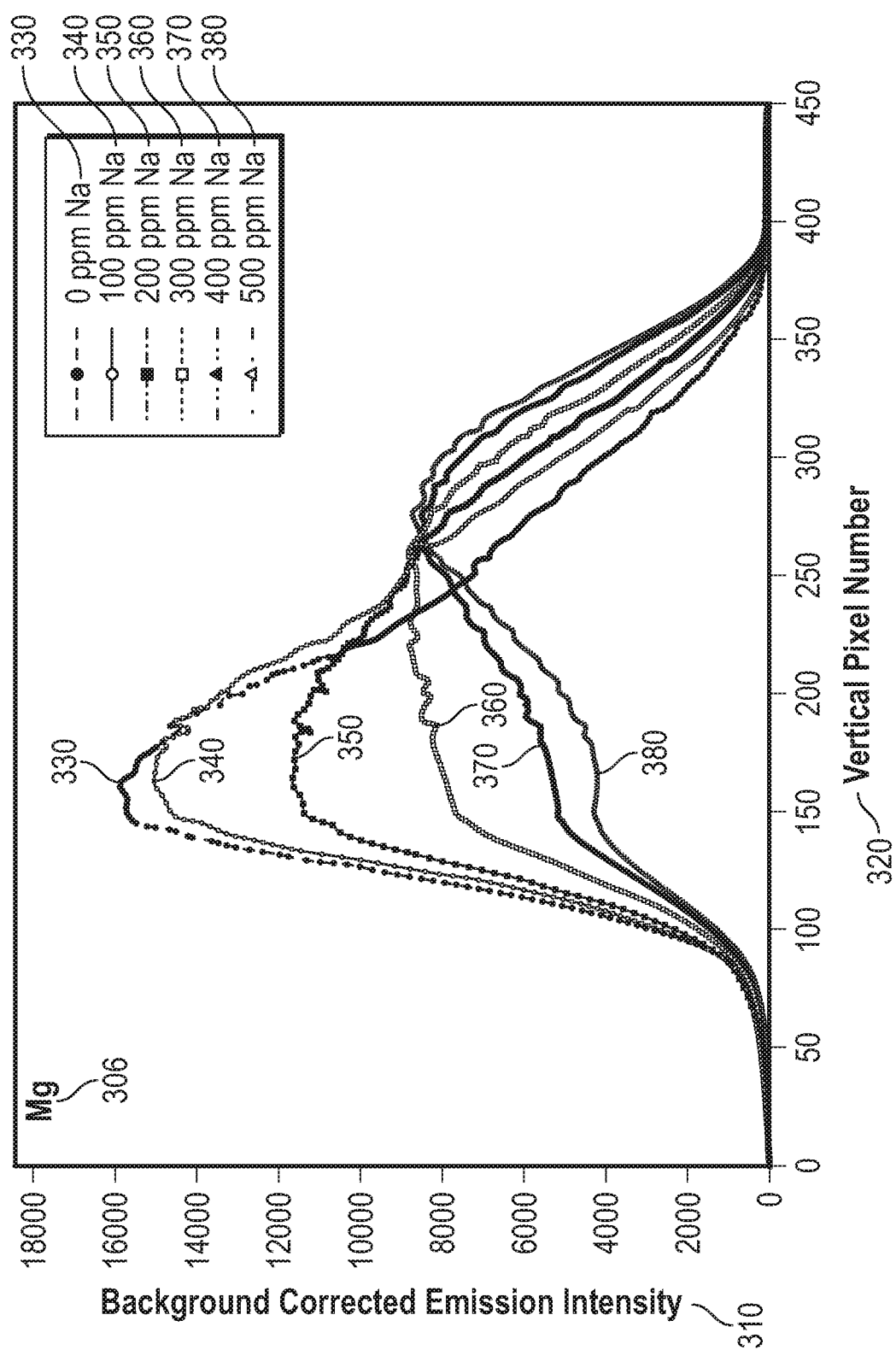
FIG. 9 depicts the 200 ppm Mg spatial emission profile with different sodium concentrations.

For the data shown in FIGS. 7-9, the background molecular emission from $N_2$ was present and contributes to the observed noise.

Spatial emission profiles for calcium, gallium, and magnesium with changing concentrations of sodium are shown in FIGS. 7-9. Background corrected emission intensity (310) is shown versus vertical pixel number (320) for changing concentrations of sodium, 0 ppm Na (330), 100 ppm Na (340), 200 ppm Na (350), 300 ppm Na (360), 400 ppm Na (370) and 500 ppm Na (380). As can be seen, the concentration of sodium has a significant impact on the spatial emission profiles. In all cases, the addition of sodium decreased the emission intensities observed lower in the plasma and increased the emission intensities higher in the plasma. Note that the position of the cathode is located near pixel 100 and the tip of the anode is located near pixel 350. The anode and cathode are separated by a distance of 3.0 mm and there is an internal magnification of 10% in the Horiba spectrometer. The individual pixel dimensions are 13.5 μm.

Figure 10:
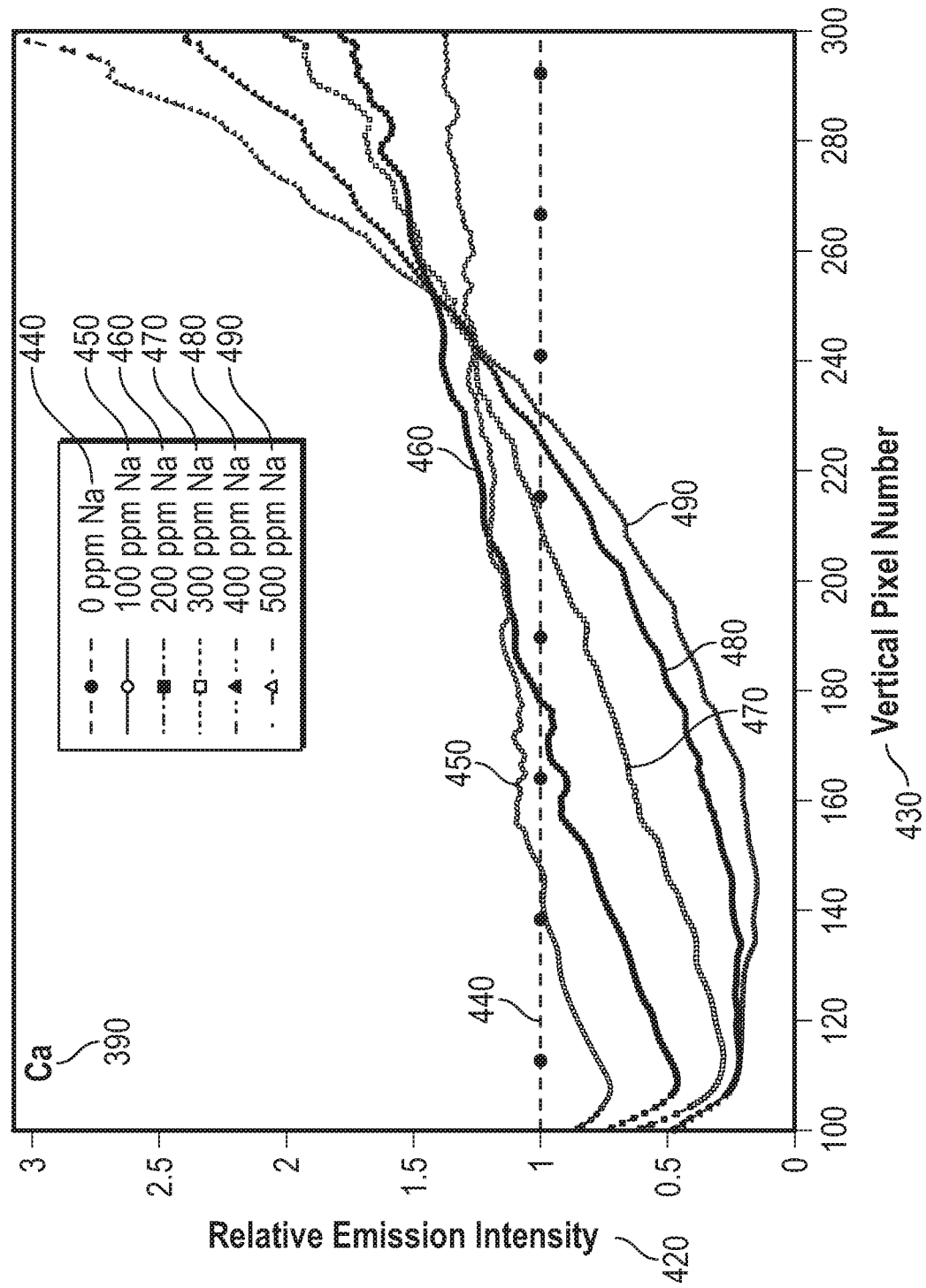
FIG. 10 depicts the relative intensity from 200 ppm Ca (signal with Na matrix divided by the signal of a matrix-free standard).
Figure 11:
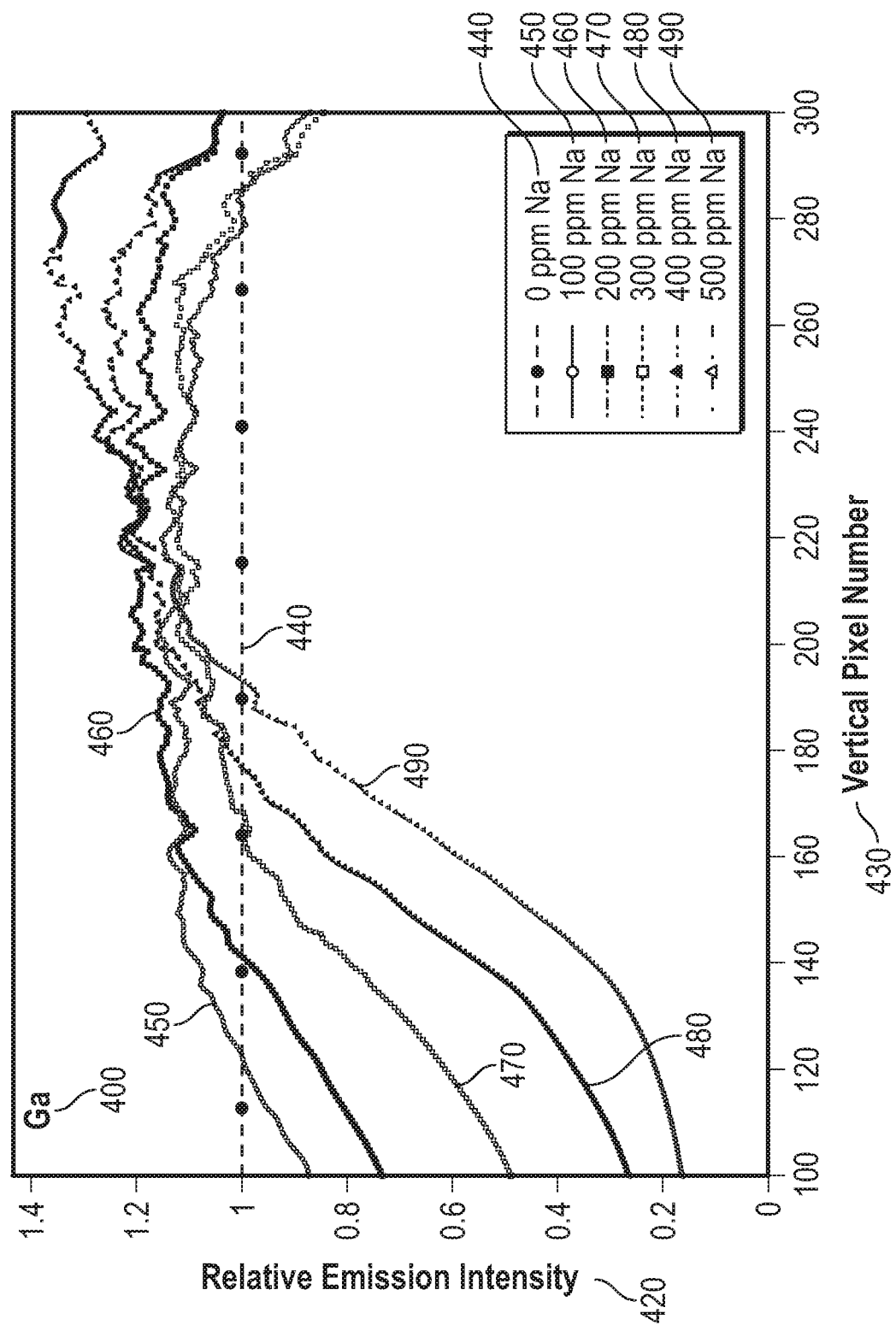
FIG. 11 depicts the relative intensity from 200 ppm Ga (signal with Na matrix divided by the signal of a matrix-free standard).
Figure 12:
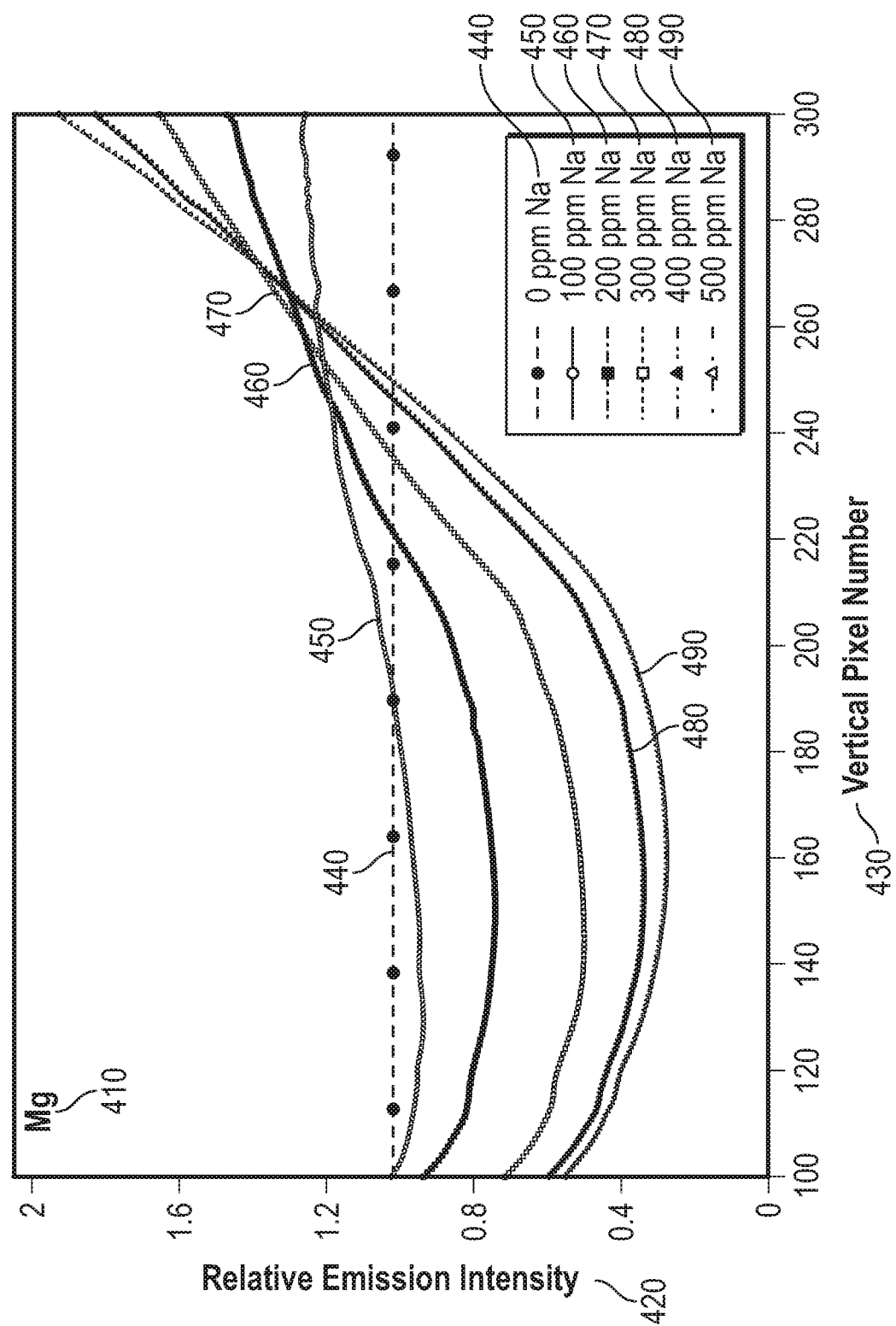
FIG. 12 depicts relative intensity from 200 ppm Mg (signal with Na matrix divided by the signal of a matrix-free standard).

Using a similar analysis as Schwartz (2016), relative intensity was calculated by dividing the signal with matrix by the signal of a matrix free standard. Relative intensity profiles are shown in FIGS. 10 to 12. A 5-point moving average was used to smooth the data. Relative emission intensity (420) is shown versus vertical pixel number (430) for increasing concentrations of sodium, 0 ppm Na (440), 100 ppm Na (450), 200 ppm Na (460), 300 ppm Na (470), 400 ppm Na (480) and 500 ppm Na (490). Increasing concentrations of sodium as the matrix modifier influence the position of the crossover point for calcium, gallium, and magnesium.

Figure 13:
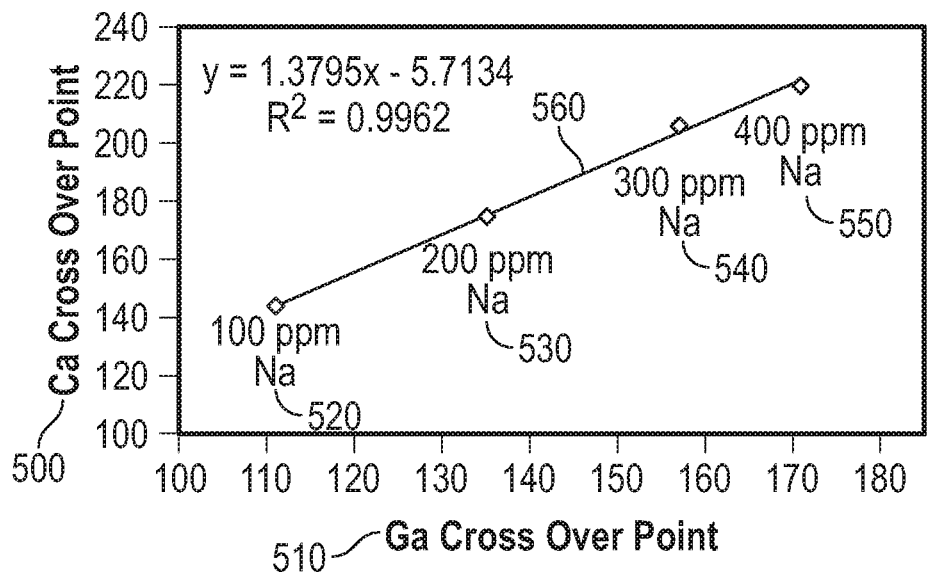
FIG. 13 depicts the correlation of Ca to Ga crossover point for concentrations of Na ranging from 100 to 400 ppm.
Figure 14:
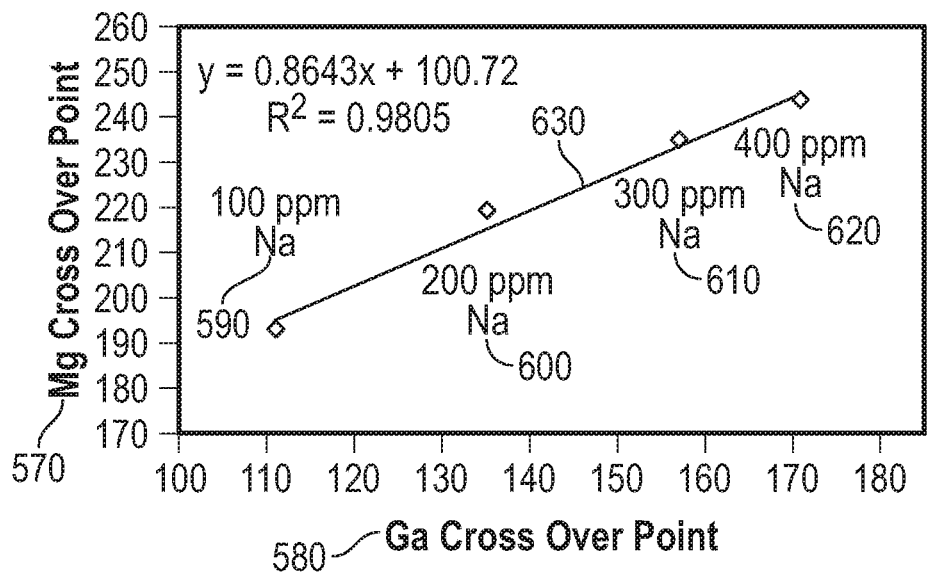
FIG. 14 depicts the correlation of Mg to Ga crossover point for concentrations of Na ranging from 100 to 400 ppm.

The correlation between the crossover points of gallium towards calcium and magnesium are shown in FIGS. 13 and 14. In FIG. 13, calcium crossover point (500) is shown versus gallium crossover point (510) for 100 ppm Na (520), 200 ppm Na (530), 300 ppm Na (540) and 400 ppm Na (550). A fit line (560) having a formula: y=1.3795x−5.7134 has an $R^2$=0.9962. In FIG. 14, magnesium crossover point (570) is shown versus gallium crossover point (580) for 100 ppm Na (590), 200 ppm Na (600), 300 ppm Na (610) and 400 ppm Na (620). A fit line (630) having a formula: y=0.8643x+100.72 has an $R^2$=0.9805.

This linear correlation will allow the spatial emission profile of an internal standard to predict the crossover points for multiple analytes. Since an internal standard can be introduced to the sample solution at a relatively high concentration, accurate spatial profiles Ca (390), Ga (400) and Mg (410) can be acquired with relatively short integration times. This provides a practical method of determining the vertical pixels to use for analyte analysis in a manner that is free from matrix interferences.

The disclosed methods and apparatus are widely applicable to the detection and measurement of the elements described herein. One example is the measurement of elements of interest in water, for example Ca or Mg in water as a measure of water hardness, which may be important for industries such as for boiler feedwater. Higher hardness of boiler feedwater may lead to increased maintenance, operating costs or downtime, for example if the water hardness leads to scaling or plugging of boiler components such as boiler tubes. Because the sodium content of boiler feedwater varies, direct measurement of Ca or Mg or both may be challenging. The disclosed methods and apparatus provide matrix management—i.e. allows measurements that are substantially free from the variable matrix interference. Referring to FIGS. 13/14 (prepared from FIGS. 7-12), one can spike the sample of boiler feedwater with an internal standard, in this example Ga, in order to determine the vertical pixel height (location) at which to obtain SCGD spectra that are free of matrix interference. Gallium is rarely, if ever present in boiler feedwater, but this can be confirmed by laboratory testing and if any problem, another appropriate internal standard can be used instead. One can observe/measure a Ga crossover point and then use FIGS. 13-14 to provide the vertical pixels to use for analyte analysis for Ca (FIG. 13) and Mg (FIG. 14). For example, if a Ga crossover point of 125 pixels is observed/measure, then the correlation of FIG. 13 indicates that using a vertical height of about 165 pixels (167 pixels using the fit formula) for Ca should be relatively free from matrix interference. The Ga crossover point of 125 pixels could be re-used, i.e. for the Mg crossover point of FIG. 14, or a fresh/renewed reading for the Ga crossover point could be obtained. If the fresh/renewed Ga crossover point is at 150 pixels because of the variable matrix (in this example sodium concentration), then the correlation of FIG. 14 indicates that using a vertical height of about 230 pixels (230 using the fit formula) for Mg should be relatively free from matrix interferences.

This disclosure provides methods, apparatus, and systems that are generally applicable to SCGD, including but not limited to be used for lab-based analysis, portable applications, on-line analysis, and any other mode of use where SCGD is involved.

Aspects of the disclosed methods, apparatus, and systems may use software code and one or more computer processors to perform certain elements or features and/or provide output and/or results.

EMBODIMENTS

Embodiments of the invention may include any combination of the features, methods, apparatus and systems shown herein, and in particular in the following numbered paragraphs. This is not to be considered a complete listing of all possible embodiments, as any number of variations can be envisioned from the description above.

Embodiment 1. A purging device for purging atmospheric gases from a solution cathode glow discharge (SCGD) apparatus, comprising a hollow body that encloses a plasma generated between a solid anode and a solution cathode, wherein the body comprises at least one opening for release of water vapor generated by the plasma.

Embodiment 2. The device of embodiment 1, wherein the body comprises a cylinder.

Embodiment 3. The device of any of the above embodiments, wherein the body has a sealed top and an open bottom.

Embodiment 4. The device of any of the above embodiments, wherein the body has a sealed top and a sealed bottom.

Embodiment 5. The device of any of the above embodiments, wherein the opening comprises one or more slots in a wall of the body.

Embodiment 6. The device of any of the above embodiments, wherein the one or more slots are adapted to allow visual observation and detection of emitted light from the SCGD.

Embodiment 7. The device of any of the above embodiments, wherein the body is a stainless steel tube.

Embodiment 8. The device of any of the above embodiments having a sealed top, wherein the sealed top comprises a plurality of pieces.

Embodiment 9. The device of any of the above embodiments having a sealed top, wherein the sealed top comprises an upper piece and a lower piece, the lower piece having a larger internal diameter than the upper piece.

Embodiment 10. A SCGD apparatus comprising a purging device of any of the above embodiments.

Embodiment 11. A method for reducing matrix interferences from a SCGD comprising: A method for reducing matrix interference in a SCGD analysis of a sample to be analyzed, wherein the sample comprises at least one element of interest, the method comprising:
 a. determining a spatial emission profile of an internal standard;
 b. determining a spatial emission profile of the at least one element of interest;
 c. determining a linear correlation between the spatial emission profile of the internal standard and the spatial emission profile of the at least one element of interest;
 d. introducing the internal standard into the sample;
 e. using SCGD analysis of the sample, measure a crossover point of the internal standard; and
 f. selecting a vertical acquisition height for SCGD analysis of the sample for the at least one element of interest from the crossover point of the internal standard using the linear correlation.

Embodiment 12. The method of embodiment 11, further comprising:
 g. obtaining a SCGD analysis of the sample, centered at about the vertical acquisition height; and
 h. measuring the emission intensity of the at least one element of interest to provide the SCGD analysis of the sample.

Embodiment 13. The method of any of the above embodiments, wherein a. to c. are performed in advance, in a calibration portion of the method and d. to h. are performed subsequently, repeatedly, continuously or semi-continuously in a measurement portion of the method.

Embodiment 14. The method of any of the above embodiments, wherein the sample comprises a variable matrix, wherein the spatial emission profile of the internal standard in a. and the spatial emission profile of the at least one element of interest in b. are determined for a plurality of conditions of the variable matrix, wherein the crossover point in e. is a matrix-free crossover point, independent of the variable matrix, and wherein the crossover point in f. is the matrix-free crossover point.

Embodiment 15. The method of any of the above embodiments, wherein the variable matrix comprises variable sodium (Na) concentration.

Embodiment 16. The method of any of the above embodiments, wherein the internal standard or the at least one element of interest or both comprise an alkali-metal cation.

Embodiment 17. The method of any of the above embodiments, wherein the internal standard comprises Ga and is substantially free of Ca and Mg, and wherein the at least one element of interest comprises Ca or Mg or both.

Embodiment 18. The method of any of the above embodiments, wherein the sample comprises boiler feedwater.

Embodiment 19. The method of embodiment 18, further comprising determining a water hardness of the boiler feedwater from a concentration of Ca or Mg or both.

Embodiment 20. The method of any of the above embodiments, further comprising providing a SCGD apparatus of any of the above embodiments, wherein the SCGD analysis is performed using the SCGD apparatus.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A self-purging device for purging atmospheric gases from a solution cathode glow discharge (SCGD) apparatus, comprising a hollow body that encloses a plasma generated between a solid anode and a water solution cathode, wherein the body comprises at least one opening extending across the entire region between the solid anode and the water solution cathode for release of water vapor generated by the plasma and for viewing the plasma across the entire region between the solid anode and the water solution cathode.

2. The device of claim 1, wherein the body comprises a cylinder.

3. The device of claim 1, wherein the body has a sealed top and an open bottom.

4. The device of claim 1, wherein the body has a sealed top and a sealed bottom.

5. The device of claim 1, wherein the opening comprises one or more slots in a wall of the body.

6. The device of claim 5, wherein the one or more slots are adapted to allow visual observation and detection of emitted light from the SCGD across the entire region between the solid anode and the water solution cathode.

7. The device of claim 2, wherein the body is a stainless steel tube.

8. The device of claim 4, wherein the sealed top comprises a plurality of pieces.

9. The device of claim 8, wherein the sealed top comprises an upper piece around the solid anode resting on a lower piece, the lower piece having a larger internal diameter than the upper piece, providing an annular gap between the internal diameter of the lower piece and the solid anode, wherein relative horizontal movement between the upper piece and the lower piece is provided.

10. A SCGD apparatus comprising the device of claim 6.

* * * * *